United States Patent
Sodo

(10) Patent No.: US 10,687,924 B2
(45) Date of Patent: Jun. 23, 2020

(54) COUPLING DEVICE FOR CONNECTING A WATER POWERED APPARATUS TO A FAUCET

(71) Applicant: INIZIATIVA CENTRO SUD S.R.L., Naples (IT)

(72) Inventor: Diego Sodo, Naples (IT)

(73) Assignee: INIZIATIVA CENTRO SUD S.R.L., Naples (IT)

(*) Notice: Subject to any disclaimer, the term of this patent is extended or adjusted under 35 U.S.C. 154(b) by 1001 days.

(21) Appl. No.: 14/902,937

(22) PCT Filed: Jul. 4, 2014

(86) PCT No.: PCT/IB2014/062872
§ 371 (c)(1),
(2) Date: Jan. 5, 2016

(87) PCT Pub. No.: WO2015/001533
PCT Pub. Date: Jan. 8, 2015

(65) Prior Publication Data
US 2016/0151135 A1    Jun. 2, 2016

(30) Foreign Application Priority Data

Jul. 5, 2013 (IT) .............. RM2013A0396
Jul. 12, 2013 (IT) .............. RM2013A0413

(51) Int. Cl.
*A61C 17/032* (2006.01)
*A61M 3/02* (2006.01)
(Continued)

(52) U.S. Cl.
CPC ........... *A61C 17/032* (2019.05); *A61M 3/025* (2013.01); *F16L 37/148* (2013.01); *E03C 1/108* (2013.01)

(58) Field of Classification Search
CPC ... F16L 37/48; F16L 2011/047; F16L 55/027; F16L 55/07; C02F 3/14; C02F 3/20; A61M 3/025; A61C 17/0214; E03C 1/108
(Continued)

(56) References Cited

U.S. PATENT DOCUMENTS 3,386,439 A     6/1968   Harper
5,284,582 A  *  2/1994   Yang ................. B01D 35/04
                                              285/8

(Continued)

FOREIGN PATENT DOCUMENTS

EP    0 927 850 A2   7/1999
GB    2 160 942 A    1/1986
(Continued)

OTHER PUBLICATIONS

International Search Report, dated Oct. 13, 2014, from corresponding PCT application.

*Primary Examiner* — Zachary T Dragicevich
*Assistant Examiner* — William S. Choi
(74) *Attorney, Agent, or Firm* — Young & Thompson

(57) ABSTRACT

A coupling device for connecting a water powered apparatus to a faucet having a mouth (1) to which a cylindrical aerator housing (3), has an aerator (2) and an attachment (4) of water powered apparatus. The aerator (2) has an upper cylindrical portion (12) and a lower cylindrical portion (15) that are joined together by converging arms (14) between which the ventilation openings (16) are formed for aerating flowing water. The attachment (4) of water powered apparatus is provided with connecting elements for coupling with engagement elements not integral with the aerator cylindrical housing (3).

16 Claims, 11 Drawing Sheets

(51) Int. Cl.
*F16L 37/48* (2006.01)
*E03C 1/10* (2006.01)
*F16L 37/14* (2006.01)

(58) Field of Classification Search
USPC ........ 285/5, 8, 396; 261/DIG. 22; 239/428.5
See application file for complete search history.

(56) References Cited

U.S. PATENT DOCUMENTS

| | | | |
|---|---|---|---|
| 5,385,533 A | 1/1995 | Coviello | |
| 2002/0084353 A1* | 7/2002 | Griffin | E03C 1/084 |
| | | | 239/428.5 |
| 2003/0042337 A1* | 3/2003 | Liang | F16L 37/48 |
| | | | 239/575 |
| 2006/0011748 A1* | 1/2006 | Ferrari | E03C 1/08 |
| | | | 239/428.5 |
| 2009/0230671 A1* | 9/2009 | Stein | E03C 1/086 |
| | | | 285/8 |

FOREIGN PATENT DOCUMENTS

| | | |
|---|---|---|
| IT | MI2011A001083 | 5/2001 |
| WO | 02-094119 | 11/2002 |

* cited by examiner

COUPLING DEVICE FOR CONNECTING A WATER POWERED APPARATUS TO A FAUCET

TECHNICAL FIELD

The present invention relates to a coupling device for connecting a water powered apparatus to a faucet.

BACKGROUND ART

There are in commerce many kinds of coupling for connecting to a faucet sanitary or household apparatuses that require a direct use of water: said couplings are based on screw connections, on pressure connections by hose clamps or on changes made to the faucet mouth in order to allow a connection.

It is known that household faucets in particular, and specifically bathroom and kitchen faucets, have a cylindrical housing that is generally screwed to the faucet mouth and adapted to contain an aerator. The aerator is usually inserted into the cylindrical housing from above and rarely from below; in the latter case the aerator is screwed directly to a faucet body. If the aerator is inserted from above, it rests on an abutment of the cylindrical housing. The aerator is generally composed by a mesh filter, a grill, a funnel-shaped mixing chamber and a small net. The funnel-shaped mixing chamber has side openings for the introduction of air.

A normal kit of aerator and cylindrical housing thereof does not allow a water powered apparatus to be attached to a faucet.

Generally, when one wants to connect one of these apparatuses to the faucet, he/she needs external attaching means to enable the apparatus to be connected to the faucet or he/she has to unscrew the aerator housing and add a special attachment for the specific use; he/she has to reattach the normal aerator housing after use.

By way of example, European patent application EP 0 927 850 discloses a member for the quick mounting of a gum sprinkler or the like onto a tap having a cylindrical body housing an aerator. The cylindrical body is externally provided with a thread in order to be screwed to a tap mouth and is internally provided, in its lower part, with means for the quick coupling of a connection having correspondingly shaped seats.

The same Applicant of the present patent application is the owner of the Italian patent No. 1325538, according to which an aerator housing normally screwed to the faucet mouth is replaced by another aerator housing that is adapted to be screwed externally to the faucet mouth and has in its lower part a bayonet lock that provides a secure and easy connection to a respective sanitary apparatus. Since the above bayonet lock has to be provided, the second aerator is larger than the normal component that it replaces. But this is not the biggest drawback.

U.S. Pat. No. 3,386,439 discloses an adapter that is screwed in its upper portion to a faucet mouth having an aerator housed inside it. A lower threaded portion of the adapter has a diameter smaller than the upper portion. A frusto-conical shaped portion being intermediate between the upper and lower portions, is configured to fit tightly against the surface of a cap containing a treatment liquid chamber connected with a pipe to a dental irrigator. It is clearly understood that the adapter or aerator housing on one side is connected to the faucet mouth, and on the other side to the quick attachment of the sanitary apparatus. To achieve such a connection, the adapter must have in its upper portion a thread which allows it to be screwed to the faucet mouth.

Therefore, a main problem is that the aerator housing, in which the sanitary apparatus to be connected to the faucet is inserted, must be able to be screwed at least to the majority of the faucets currently available in commerce, if not to all. However this can only be achieved by manufacturing a wide variety of aerator housings having diameters, threads for the attachment to the faucet mouth and connection means compatible with the respective household or sanitary apparatuses.

Another drawback is that the purchaser of a water powered apparatus is not always aware of the type of attachment of its own faucet and the dimensions thereof, so that he/she may be forced to forgo the purchase of a water powered household or sanitary apparatus of his/her interest.

In addition, the spread of such water powered apparatuses in welcome centres is also limited, for economic and aesthetic reasons, by the need of modifying or replacing some of the faucets.

DISCLOSURE OF THE INVENTION

The present invention aims to overcome all these drawbacks.

In particular, a main purpose of the present invention is to make substantially universal a connection of a water powered apparatus to a faucet, regardless of the shape and size of the faucet to which it must be connected.

A purpose of the present invention is to provide a filter aerator adapted to allow the connection of a water powered apparatus to a faucet by using the same aerator housing that is normally screwed to the faucet mouth.

Still another object of the present invention is to provide an aerator contained within a respective housing having dimensions smaller than those of the aerator housings provided with coupling means for the connection to a water powered apparatus.

A further object of the present invention is to provide a coupling device in which the size of the aerator housing with respect to the aerator contained therein does not hinder the connection.

The above objects are achieved by a coupling device for connecting a water powered apparatus to a faucet having a mouth to which a cylindrical aerator housing, the coupling device comprising an aerator and an attachment of water powered apparatus, the aerator having an upper cylindrical portion and a lower cylindrical portion joined together by converging arms between which the ventilation openings are formed for aerating flowing water, wherein said attachment of water powered apparatus is provided with connecting means for coupling with engagement means not integral with said aerator cylindrical housing.

In a first embodiment, these engagement means are integral with an aerator with various distinctive features according to the present invention.

In a second embodiment, these engagement means are integral with a aerator holding fitting that is interposed between the aerator housing and an aerator of a conventional type.

In accordance with the first or second embodiment, the main object of the present invention is achieved, i.e. the original aerator housing has not to be replaced for connecting a water powered apparatus.

BRIEF DESCRIPTION OF THE DRAWINGS

Further features and advantages of the invention will become apparent from the description of embodiments and variations thereof, of a coupling device for connecting a water powered apparatus to a faucet, the coupling device being illustrated by way of an indicating and not limiting example in the accompanying drawings in which.

DESCRIPTION OF EMBODIMENTS OF THE INVENTION

Figure 1:
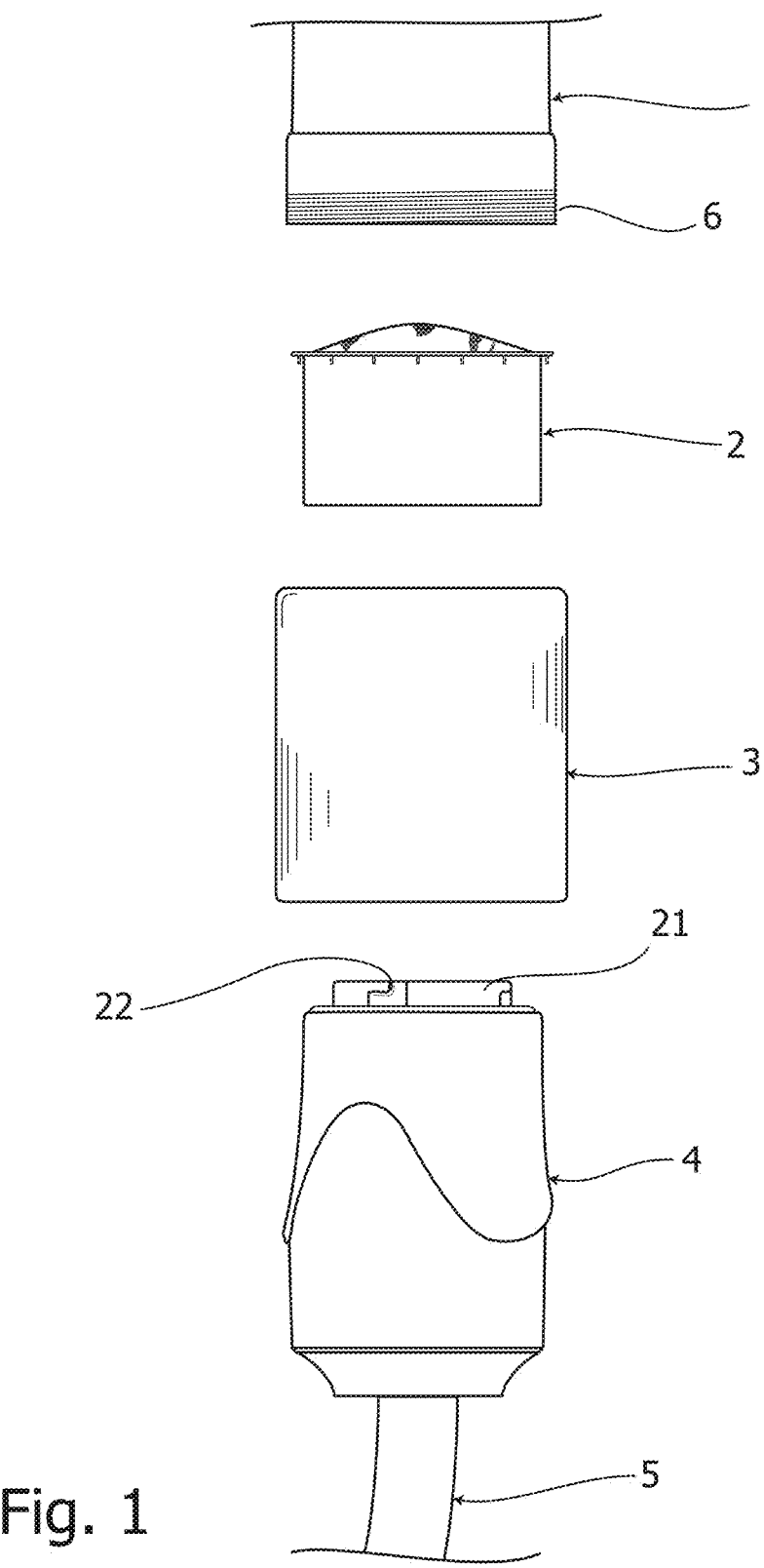
FIG. 1 is an exploded partial side view of a coupling device for connecting a water powered apparatus to a faucet according to a first embodiment of the present invention.
Figure 2:
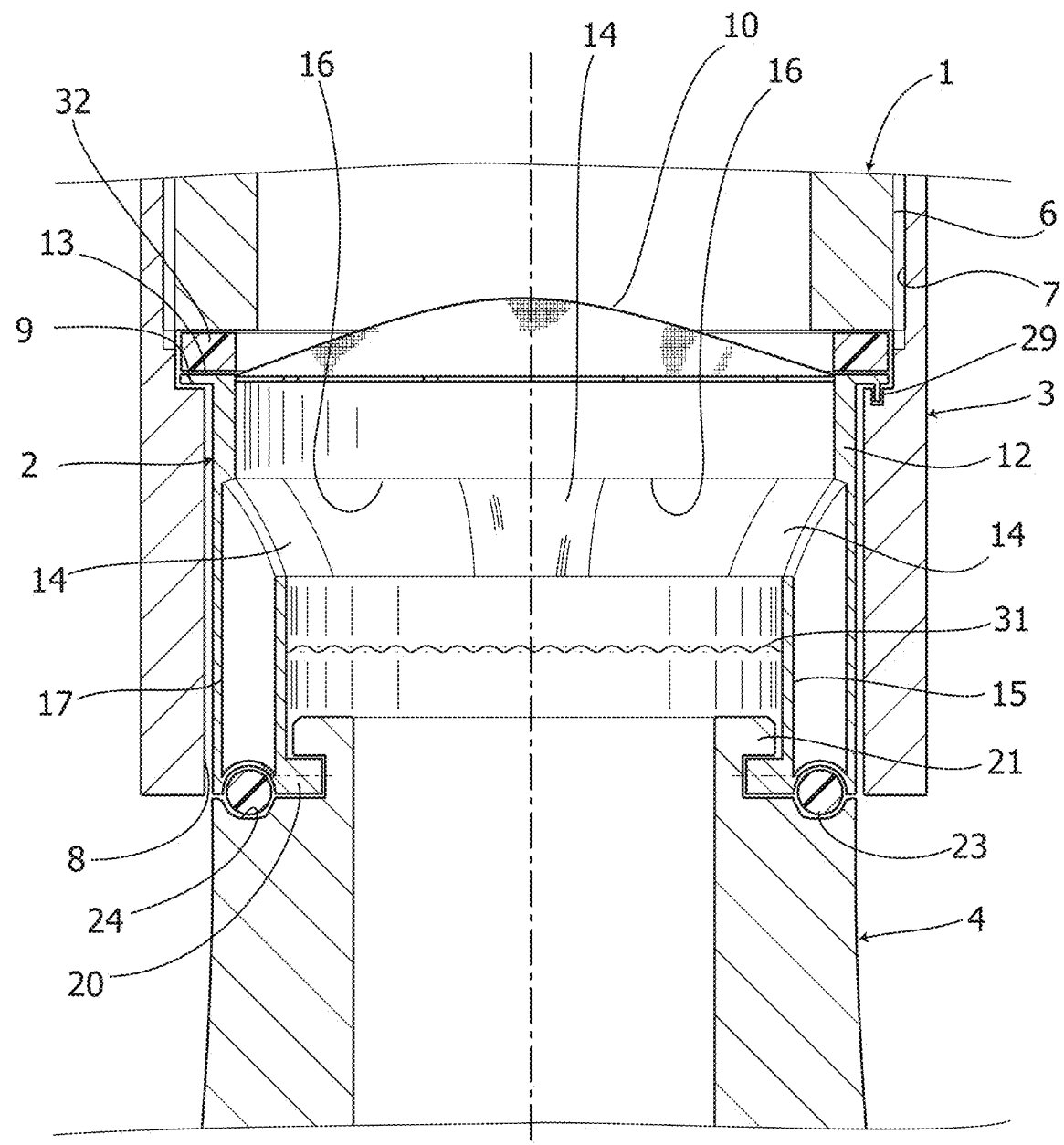
FIG. 2 is a partial axial sectional view of the coupling device in FIG. 1 in an assembled arrangement.

First, reference is made to FIGS. 1 and 2, which show an exploded side view and a partial axial sectional view respectively, of a coupling device for connecting a water powered apparatus to a faucet according to a first embodiment of the present invention. The faucet is shown later.

In FIGS. 1 and 2 there are indicated as 1 a faucet mouth, as 2 an aerator, as 3 a cylindrical aerator housing, as 4 an attachment, and as 5 a joined pipe of a water powered apparatus that is not shown in the drawings. If the water powered apparatus is a sanitary apparatus, it could be a water-jet apparatus for interdental cleaning, an intestinal or vaginal washing apparatus, a water powered toothbrush, or other.

The aerator 2 is conventionally contained within the cylindrical housing 3 which is mounted at the mouth 1 thanks to a thread, for example, an external thread 6 on the faucet mouth 1, and a corresponding internal thread 7 formed in the wall 8 of the cylindrical housing 3. Formed below the internal thread 7, on the inner side of the wall 8, is a stepped portion 9.

Figure 3:
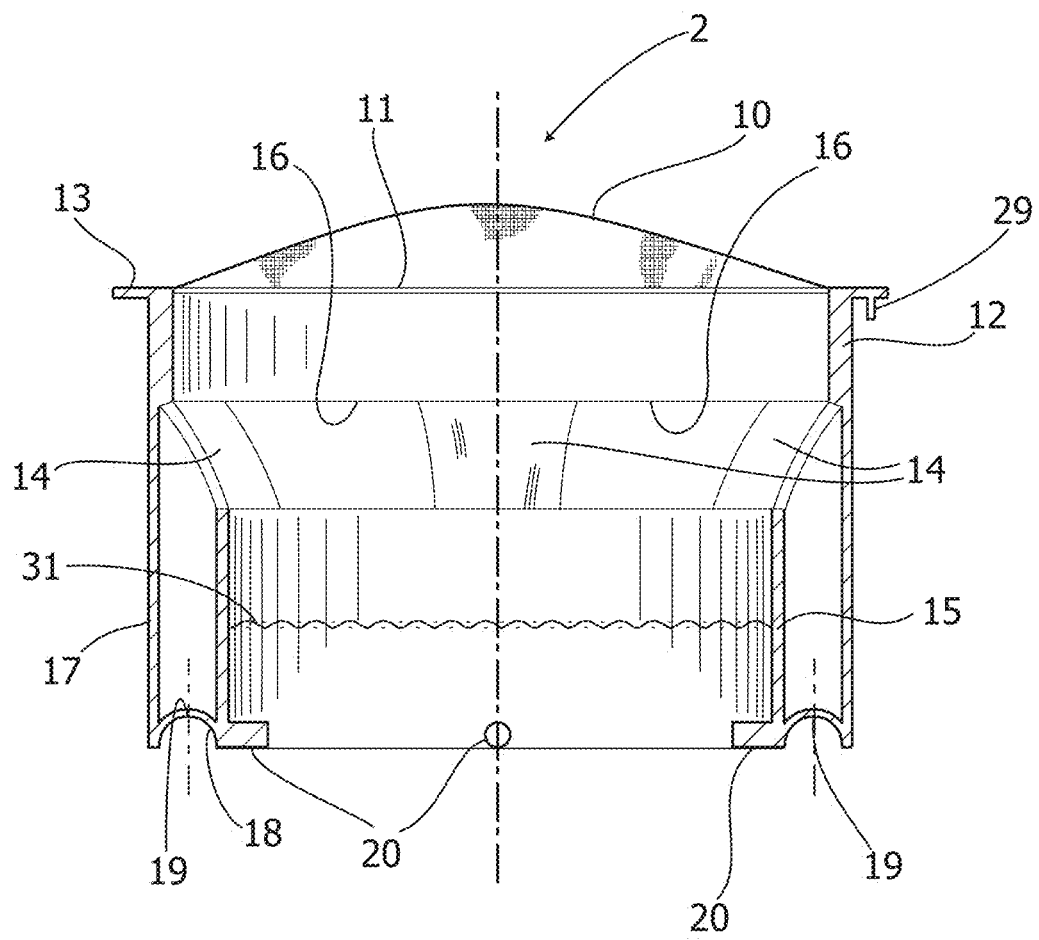
FIG. 3 is an axial sectional view of the aerator only of the coupling device in FIG. 1.

The aerator 2, also shown in an axial sectional view in FIG. 3, has conventionally, starting from the top down, an upward convex mesh filter 10 and a first perforated wall 11, the one and the other being integral with a first, or upper, cylindrical portion 12 radially projecting with a flange 13.

Converging arms, generically indicated as 14, connect the upper cylindrical portion 12 with a second, or lower, cylindrical portion 15 having a diameter smaller than that one of the first cylindrical portion 12. Terms as "upper" and "lower" refer to the normal flow of water out of the faucet. The first and second cylindrical portions 12, 15 are then funnel arranged thanks to the converging arms 14. Ventilation openings 16 for aerating the flowing water are between an arm and the other.

According to the first embodiment of the invention, the aerator 2 has a cover 17 extending downwards from the first cylindrical portion 12 and externally concentrical to the second cylindrical portion 15. The second cylindrical portion 15 and the cover 17 are joined at the bottom by a downward concave circular crown 18. The circular crown 18 is equipped with a succession of through holes 19 having vertical axis.

Furthermore, according to the first embodiment of the invention shown in FIGS. 1 to 3, radial pins 20, for example four in number, are provided protruding inwardly from the second cylindrical portion 15.

As shown in FIG. 2, the aerator 2 is supported on the wall 8 of the cylindrical housing 3 by means of the stepped portion 9 on which the aerator 2 rests with its flange 13. The flange 13 is retained in position by the faucet mouth 1 with the interposition of a gasket 32. The aerator 2 is prevented from rotating also thanks to anti-rotation means between the flange 13 and the stepped portion 9. By way of example, such anti-rotation means may be in the form of pins 29 formed in the flange 13 of the aerator 2, and corresponding holes formed in stepped portion 9 of the cylindrical housing 3. In case of need, when the inner diameter of the cylindrical housing 3 is very large, disks can be expected to be placed on the stepped portion 9 to allow the support of an aerator 2 having a diameter less than the internal diameter of the cylindrical housing 3. Such disks, known per se, are not shown in the drawings.

When the aerator 2 is positioned in the housing cylindrical 3 as above described and shown in FIG. 2, the radial pins 20 serve as engagement means for the bayonet lock with the attachment 4 of the water powered apparatus, which could be household or sanitary and is not shown in the drawings. The attachment 4 has a collar 21 externally provided with L-shaped grooves indicated as 22. When coupling the aerator 2 and the attachment 4 of the water powered apparatus, the radial pins 20 of the aerator 2 are inserted in the L-shaped grooves 22 of the collar 21 and, with a small rotation, complete the lock perfected by an O-ring 23 that is suitably housed in a circular recess 24 of the attachment 4. It should be noted that the outer diameter of the attachment 4 according to the invention is always less than the internal diameter of the cylindrical housing so that the attachment 4 does not hinder the lock in cases in which the length of the cylindrical housing is greater than that one of the aerator contained inside.

When the above described coupling with a water powered apparatus is not present, the aerator 2 normally functions as such, without any need to be disassembled from the faucet mouth 1. It should be understood that the attachment of the water powered apparatus no longer depends on the shape and dimensions of the faucet, but only on the assembly compatibility of the aerator 2 according to the invention within the cylindrical housing 3 of a traditional type mounted on the faucet mouth 1. This makes more versatile, substantially universal, the attachment of the sanitary or household apparatus since the aerator 2 is made so as to be dedicated to their own particular water powered apparatus to which it is connected.

Figure 4:
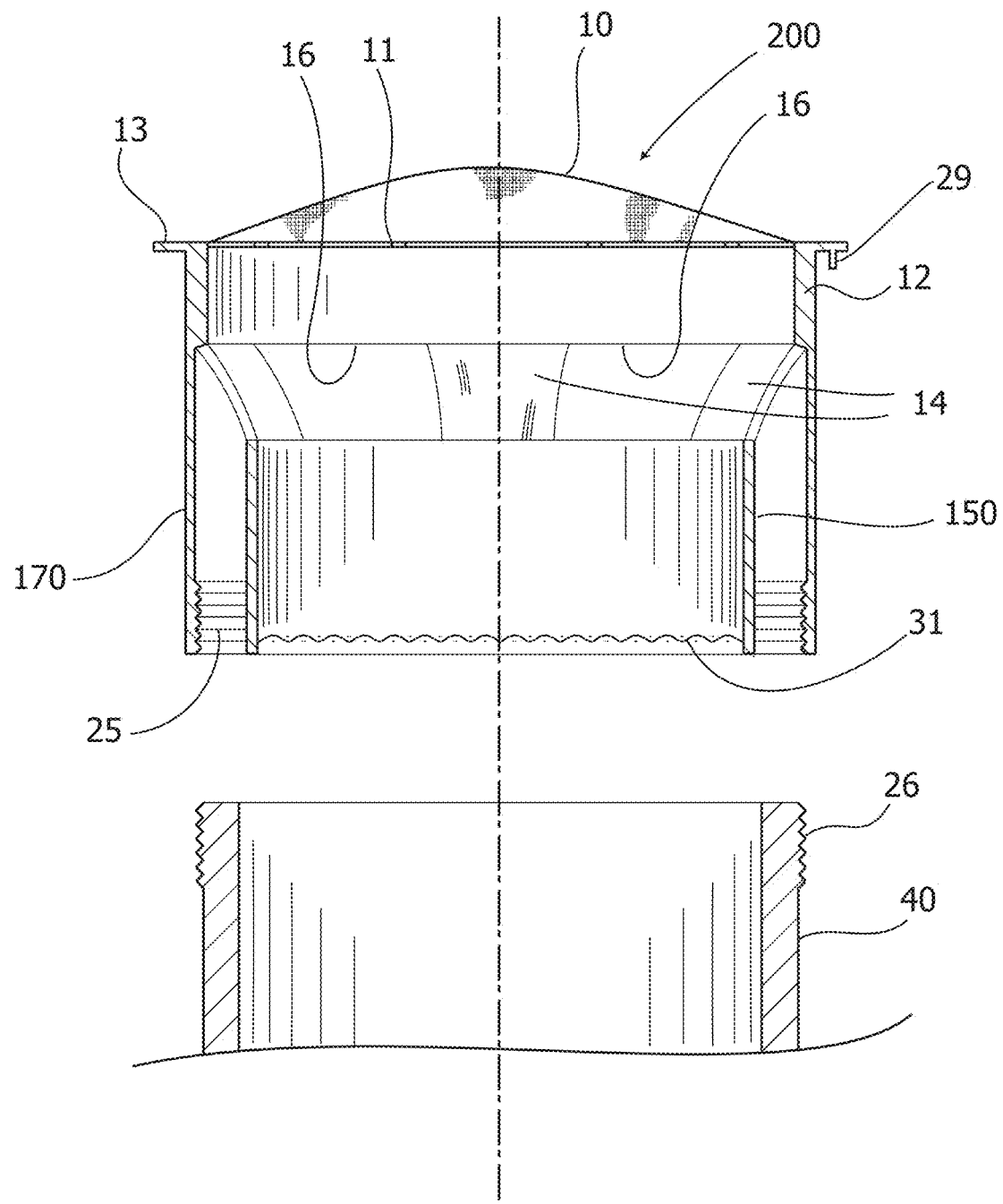
FIG. 4 is an axial sectional view of the aerator and of a part of the coupling device for connecting a water powered apparatus in accordance with a first variant of the first embodiment of the invention.
Figure 5:
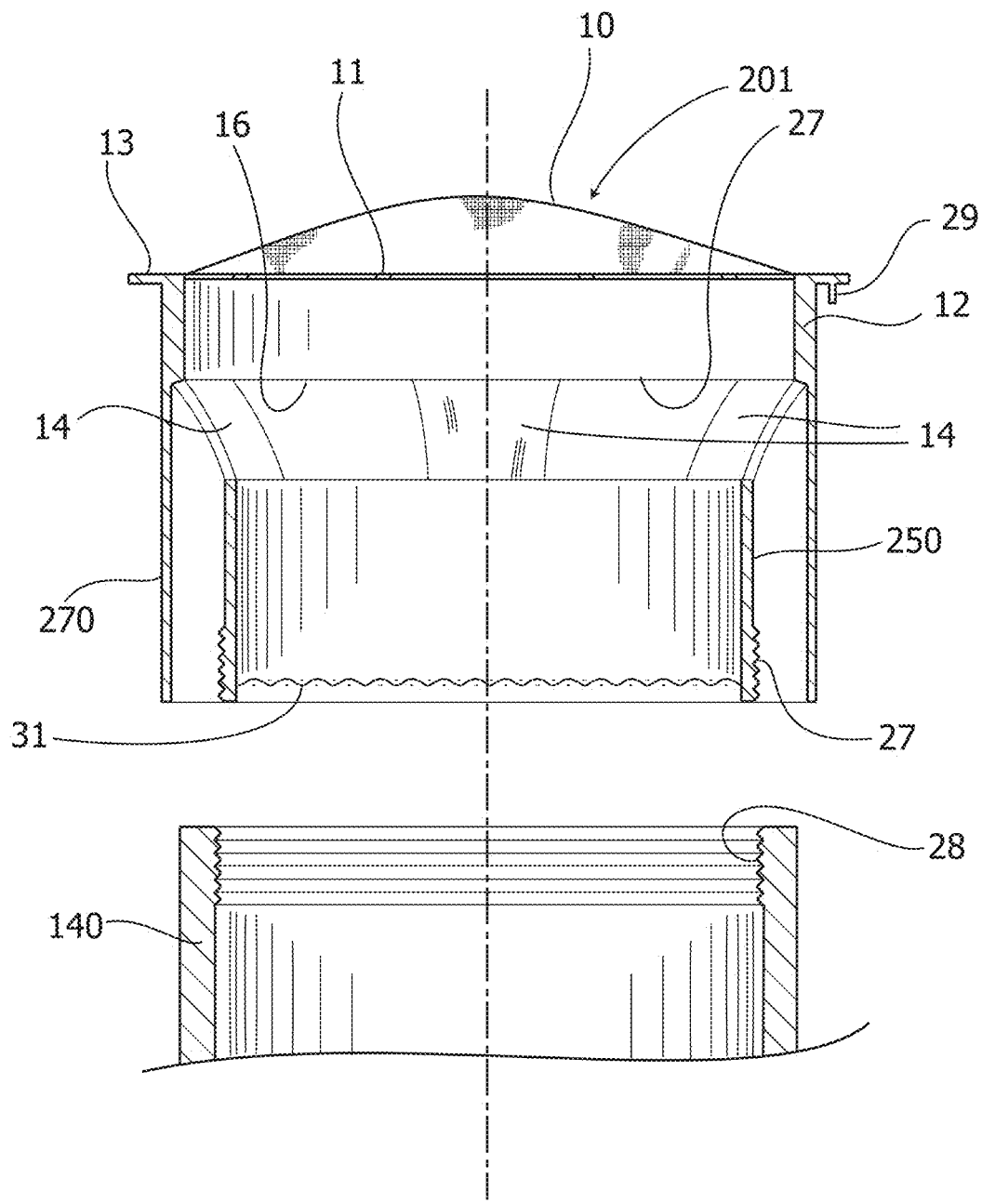
FIG. 5 is an axial sectional view of the aerator and of a part of the coupling device for connecting a water powered apparatus to a faucet in accordance with a second variant of the first embodiment of the invention.

Shown in FIGS. 4 and 5 are axial sectional views of the aerator and of part of the attachment of a water powered apparatus according to a first variant of the first embodiment of the invention.

The same or similar reference numerals are used to represent parts identical or similar to those of the first embodiment in FIG. 3.

With reference to the first variant of the first embodiment in FIG. 4, the description of the already illustrated parts of an aerator 200 is not repeated here. Their differences are only highlighted.

It can be noted that a female thread 25 is formed on a cover 170, and differently from the first embodiment the second cylindrical portion 150 is not connected to the cover 170.

In this way it is possible to screw the attachment 40 of the water powered apparatus to the mantle 170. The attachment 40, shown only partially, is provided with a male thread 26 engageable with the female thread 25 of the cover 170. Indicated as 31 is a small net that is normally present in all the aerators.

With reference to the second variant of the first embodiment in FIG. 5, an aerator 201 is shaped with a cover 270 and with a second cylindrical portion 250 provided with an external thread 27. Thanks to this configuration it is possible to screw on the second cylindrical portion 250 an attachment 140, which is also shown only partially, and equipped with an internal thread 28 engageable with the external thread 27 of the second cylindrical portion 250.

Figure 6:
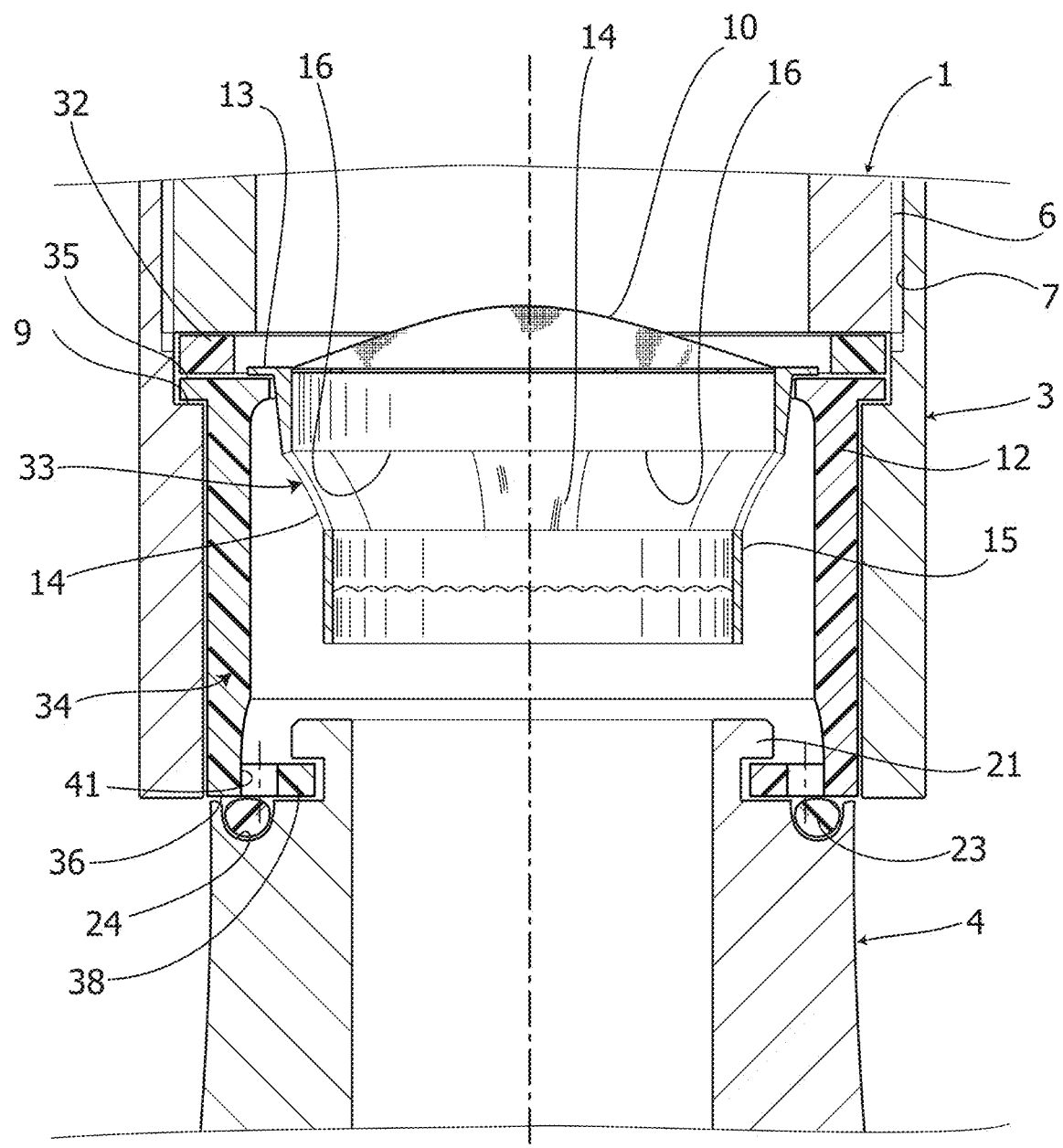
FIG. 6 is a partial axial sectional view of the coupling device according to a second embodiment of the present invention.
Figure 7:
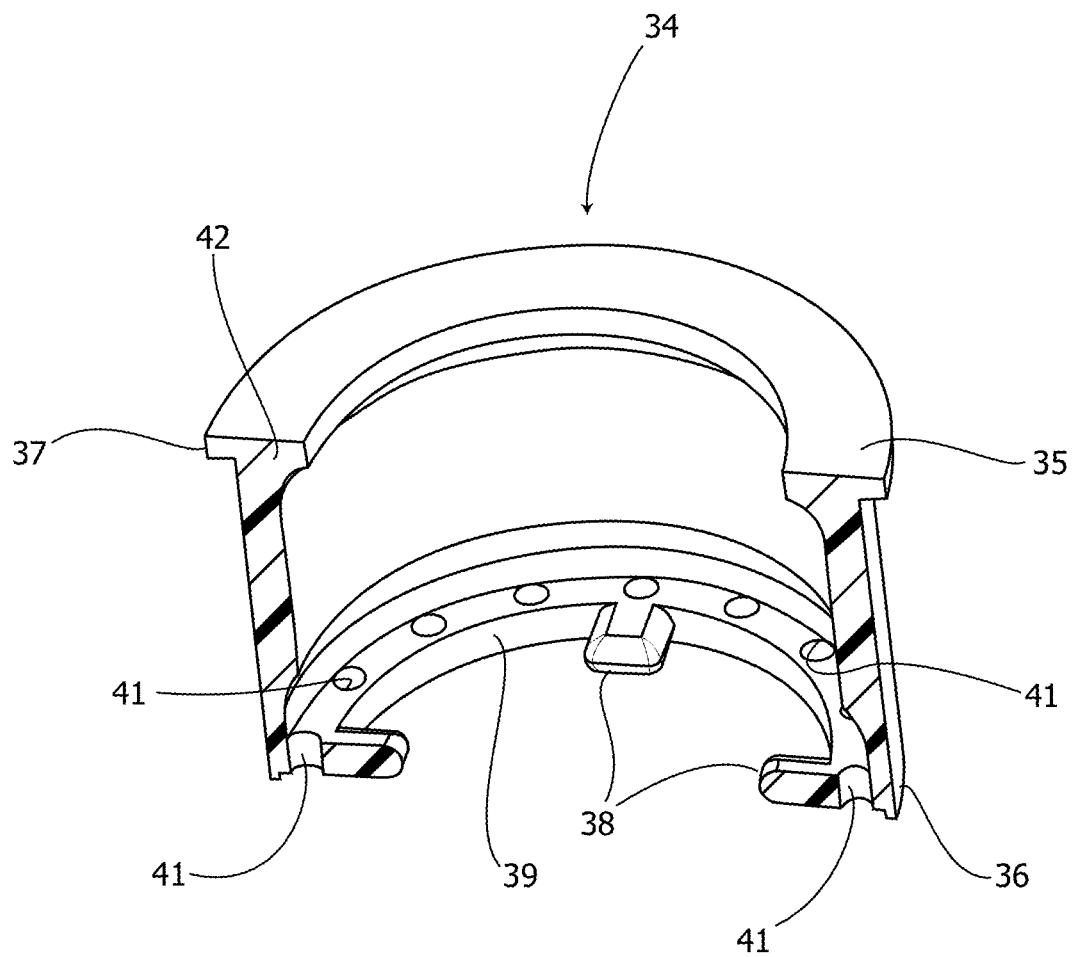
FIG. 7 is an axial sectional perspective view of an aerator holder fitting of the coupling device in FIG. 6.
Figure 8:
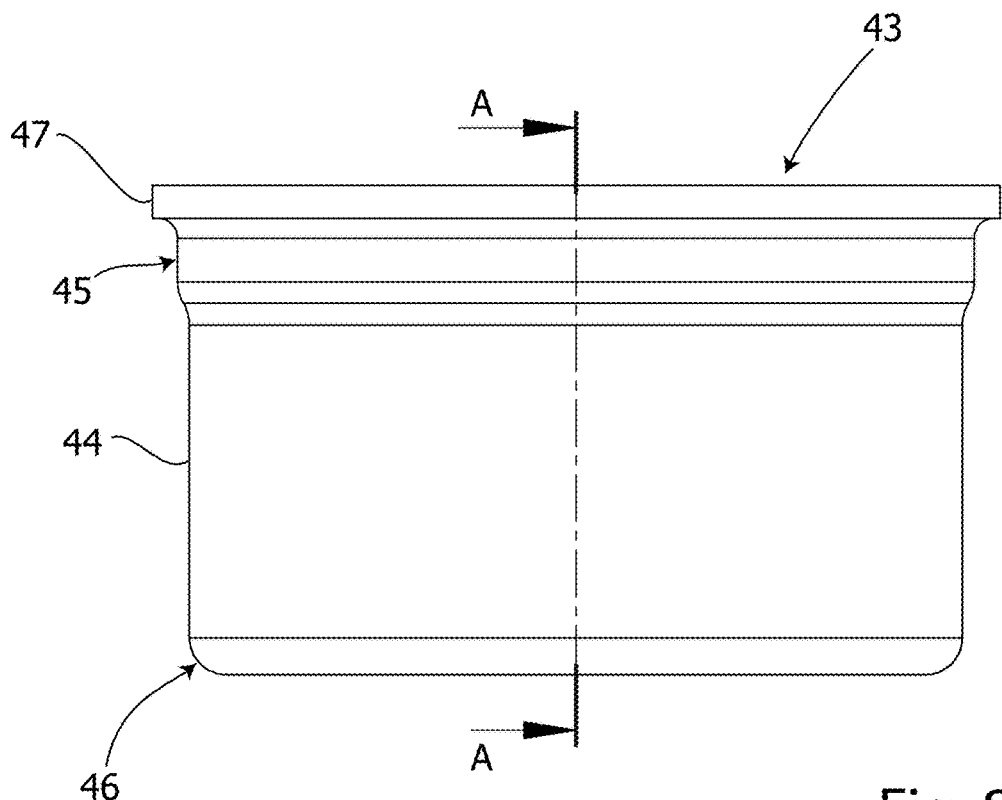
FIG. 8 is a side view of a variant of the aerator holder fitting of the second embodiment of the present invention.
Figure 9:
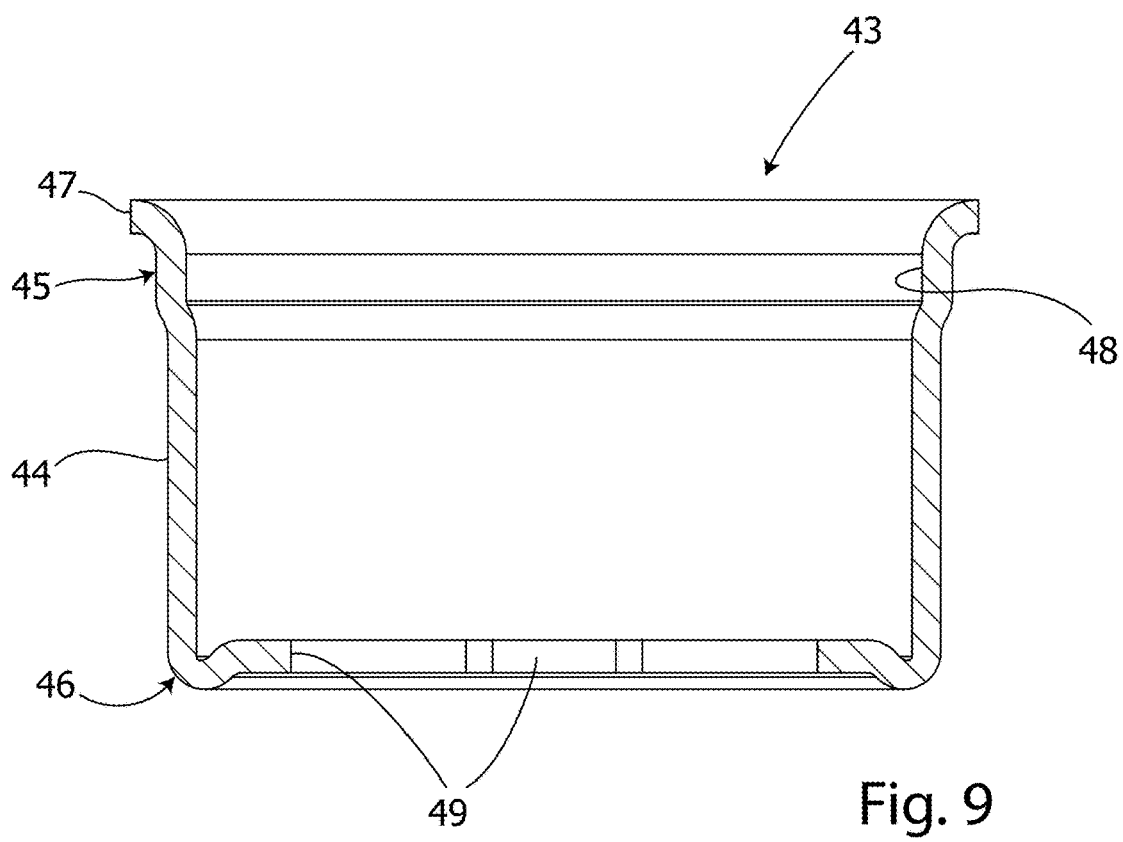
FIG. 9 is a cross-section view along line A-A of the aerator holder fitting in FIG. 8.
Figure 10:
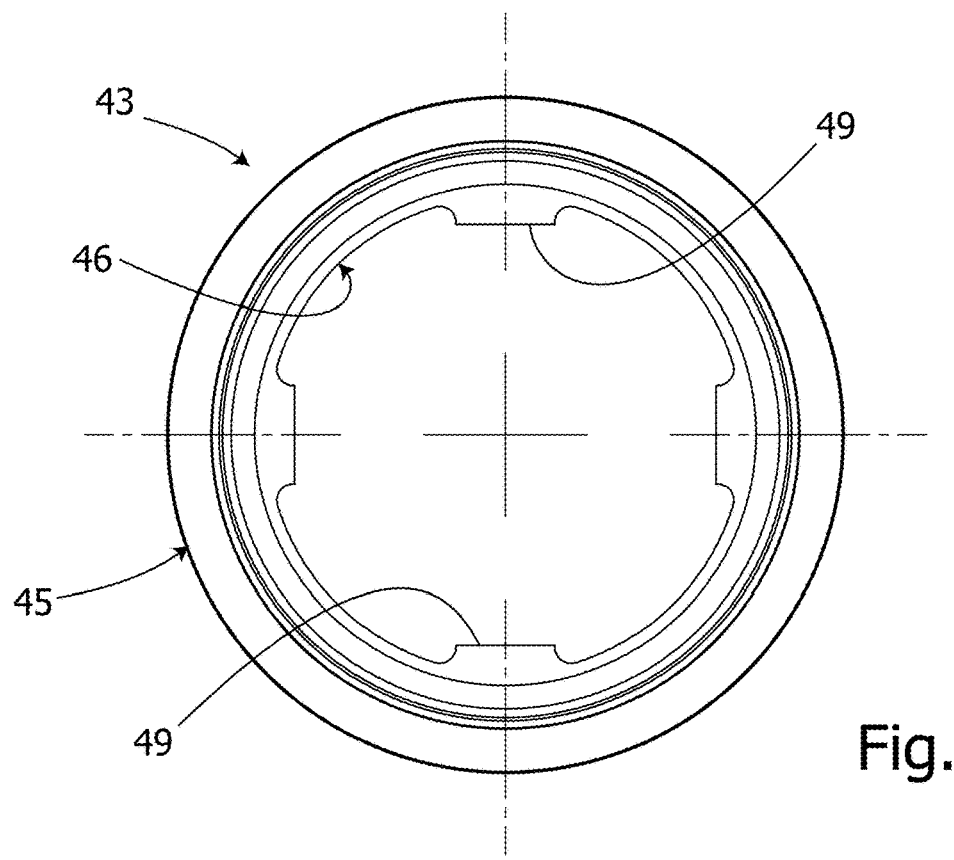
FIG. 10 is a top plan view of the aerator holder fitting in FIG. 8.
Figure 11:
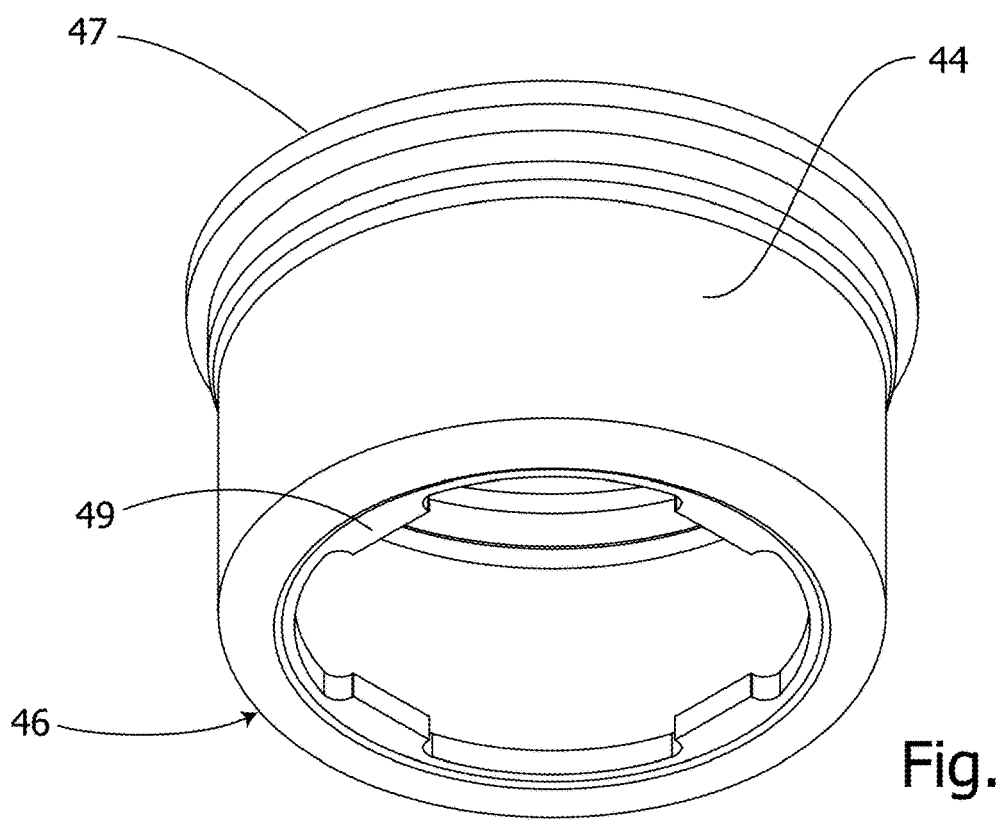
FIG. 11 is a bottom perspective view of the aerator holder fitting in FIG. 8.

Reference is made now to FIG. 6, which is a partial axial sectional view of a second embodiment of the coupling device according to the invention. In FIG. 6 equal parts are indicated with the same reference numerals in FIG. 2 of the first embodiment. As it is evident, the aerator indicated as 33 is of a conventional type, and it does not rest with its flange 13 on the stepped portion 9 of the cylindrical housing 3, but on an aerator holder fitting 34. The aerator holder fitting 34, which is shown alone in a perspective view in FIG. 7, rests on the stepped portion 9 of the cylindrical housing 3 that in turn is mounted, by means of threaded couplings 6, 7 on the faucet mouth 1.

The aerator holder fitting 34, which is normally made by molding plastic material in the shape of the tubular sleeve, has an upper end 35 and a lower end 36. The upper end 35 of the aerator holder fitting 34 is equipped with an annular protrusion 37 facing radially outwards in such a way that the upper end 35 is supported by the stepped portion 9 of the cylindrical housing 3 acting as an abutment. The lower end 36 is provided with radial pins 38 protruding radially inwardly in the aerator holder fitting 34. In the embodiment shown the radial pins 38 are in one piece with a circumferential edge 39 projecting inwardly from the lower end 36 of the aerator holder fitting 34.

The annular protrusion 37 has a downwards facing surface provided with a engagement means for engaging the stepped portion 9 of the cylindrical housing 3. Such engagement means, not shown in the drawings, can be constituted by recesses and protrusions in the shape of teeth or by a simple surface roughness which increases the contact friction, useful to prevent relative rotation of the aerator holder fitting 34 with respect to the cylindrical housing 3, when the attachment 4 of a water powered apparatus (not shown) is coupled to the aerator holder fitting 34 at the lower end 36 thereof. The attachment 4 is provided with corresponding connecting means already described with reference to the first embodiment.

Alternatively to the radial pins 38 that are useful for a bayonet lock, equivalent connecting means may be provided, such as an internal thread engageable with an external counter thread (both not shown).

The circumferential edge 39 of the aerator holder fitting 34 has also the purpose of constituting a sealing abutment for an O-ring of the attachment 4 of the water powered apparatus. This sealing abutment has a series of holes 41 or, alternatively, a jagged or sinusoidal pattern, not represented, in order to allow the passage of air when the attachment 4 of the water powered apparatus is decoupled, and the aerator 33 functions as such.

It is reiterated that the aerator 33 is of a conventional type and therefore it is not further described. It rests with its flange 13 on an inner annular ledge 42 of the upper end 35 of the aerator holder fitting 34.

The through holes 41 are useful in the presence of the aerator 33 to allow the traditional air circulation. It should be evident that the function of aeration of the water is substantially absent when an attachment 4 of a water powered apparatus is coupled to the aerator holder fitting 34.

When the attachment 4 is removed, the aerator 33 carries out its normal function.

Reference is made now to FIGS. 8 to 11 which are a side view, a cross section view, a top plan view and a bottom perspective view respectively, of a variant of the aerator holder fitting according to the second embodiment of the present invention.

This variant of the aerator holder fitting, generally indicated as 43, is preferably made by deep drawing of metal material. For this reason it has a more economical manufacture than the aerator holder fitting 34 described above with reference to FIGS. 6 and 7.

The aerator holder fitting 43 is substantially cylindrical as it has a tubular wall 44 with an upper portion 45 and a lower portion 46. The upper portion 45 of the aerator holder fitting 43 is provided with an annular protrusion 47 facing radially the outside in order that it is supported by the abutment stepped portion 9 of the cylindrical housing 3, in the same way of the aerator holder fitting 34 of the second embodiment. Furthermore, the upper portion 45 of the aerator holder fitting 43 protrudes with respect to the tubular wall 44 in order to form a seat 48 for a conventional type of aerator. The lower portion 46 of the aerator holder fitting 43 is provided with radial projections 49 facing radially inward in the aerator holder fitting 43.

Figure 12:
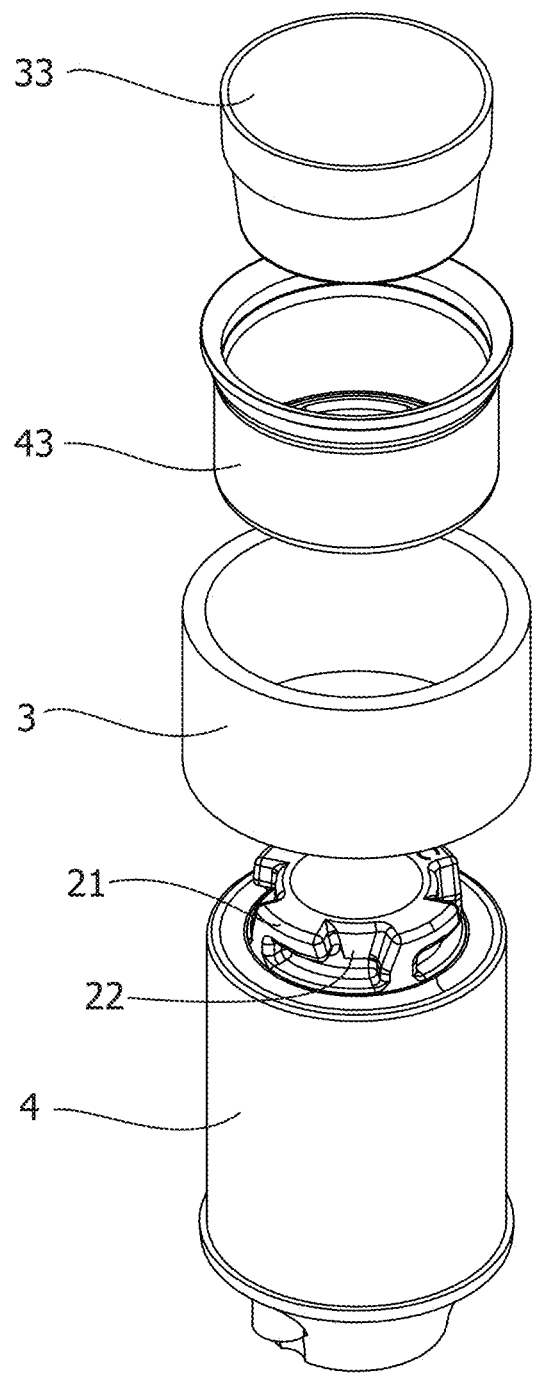
FIG. 12 is an exploded schematic perspective view from above of a coupling device for connecting a water powered apparatus to a faucet that employs the aerator holder fitting in FIG. 8.

FIG. 12 is an exploded perspective view from above of a coupling device for connecting a water powered apparatus to a faucet that employs the aerator holder fitting 43 shown in FIGS. 8 to 11.

Denoted as 33 in FIG. 12 is an aerator 33 of conventional type, as 43 the aerator holder fitting 43, as 3 the cylindrical housing and as 4 the attachment for water powered apparatus. The attachment 4 presents the collar 21 provided externally with L-shaped grooves indicated as 22.

Traditionally provided on the attachment 4 is the seat for an O-ring not shown.

Figure 13:
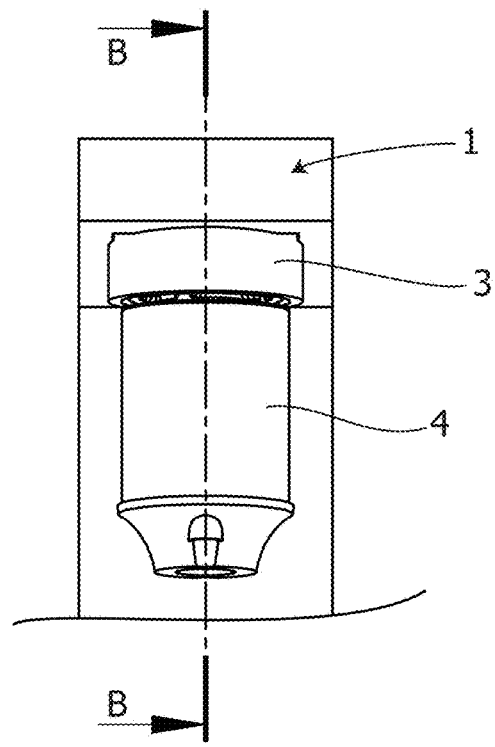
FIG. 13 is a partial side view of the coupling device in FIG. 12 in an arrangement assembled and mounted on a faucet mouth.
Figure 14:
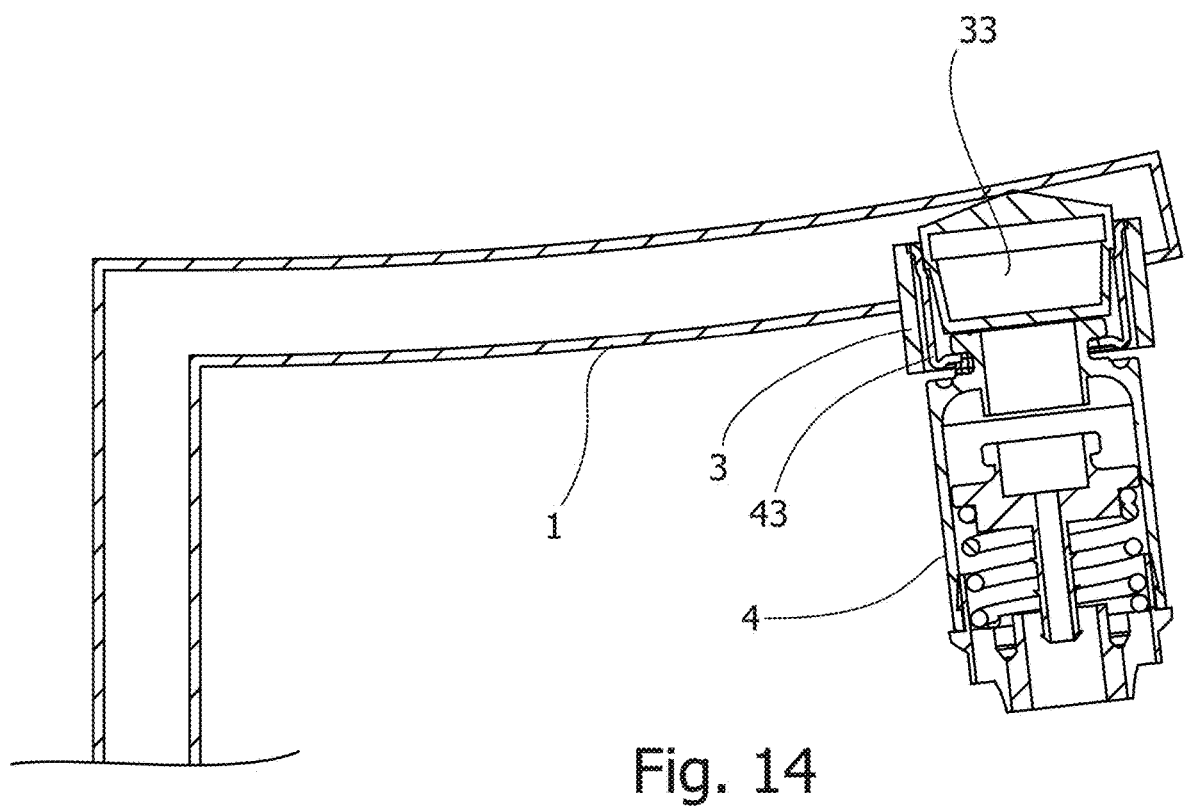
FIG. 14 is a cross-section view according to line B-B in FIG. 13.

Reference is made now to FIGS. 13 and 14 which are a partial side view of the coupling device in FIG. 12 in an arrangement assembled and mounted to a faucet mouth 1 and a cross-section obtained along the line B-B in FIG. 13, respectively.

As shown in FIG. 14, the aerator 33 is placed on the aerator holder fitting 43 that in turn rests on the stepped portion 9 of the cylindrical housing 3, which is screwed to the mouth of the tap 1. The attachment 4 of the water powered apparatus engages radial projections 49 of the aerator holder fitting 43. The attachment 4 is not described in detail since it is of a conventional type.

It is understood that the intended objects are achieved by the invention. In particular, the connection of a water powered sanitary or household apparatus is made substantially universal, regardless of the shape and size of the faucet to which said apparatus must be connected. Thanks to the second embodiment described above, this object is achieved by using normal aerators in commerce.

The characteristics of the coupling device according to the present invention may be different from those described above, and all modifications and variations fall within the scope of the appended claims.

The invention claimed is:

1. A coupling device for connecting a water powered apparatus to a faucet having a mouth to which a cylindrical aerator housing having a stepped portion is mounted, the coupling device comprising:
  an aerator, which is located inside the cylindrical aerator housing, the aerator including
    i) an upper cylindrical portion,
    ii) a lower cylindrical portion,
    iii) arms that join the upper cylindrical portion to the lower cylindrical portion, the arms converging in a water flow direction, and
    iv) ventilation openings located between the arms, the ventilation openings for aerating flowing water;
  an aerator holder fitting mounted inside the cylindrical aerator housing resting on the stepped portion of the cylindrical aerator housing;
  engagement means integral with the aerator holder fitting; and
  an attachment for water powered apparatus,
  said attachment for water powered apparatus including connecting means for coupling with the engagement means of the aerator holder fitting,
  wherein a top of said aerator is provided with a flange which is sustained by the aerator holder fitting supported by the stepped portion of said cylindrical aerator housing,
  wherein said aerator holder fitting includes the engagement means that couples to said connecting means of the attachment for water powered apparatus, and
  wherein said engagement means of the aerator holder fitting are a plurality of inwards projecting radial pins, and said connecting means of the attachment for water powered apparatus are in the form of L-shaped grooves.

2. The coupling device according to claim 1, wherein the aerator has a cover which is equipped at the top with a flange for resting on said portion step of cylindrical aerator housing and extends downward from said upper cylindrical portion and externally concentrical to said lower cylindrical portion.

3. The coupling device according to claim 2, wherein said lower cylindrical portion and the cover are connected at the bottom by a circular crown that is concave downward and is provided with a plurality of through holes having vertical axis, radial pins being provided protruding inwardly from the lower cylindrical portion of said aerator as engagement means for a bayonet lock with connecting means in the form of corresponding L-shaped grooves formed in a collar of said attachment for water powered apparatus.

4. The coupling device according to claim 2, wherein an internal thread as engagement means of said aerator is made in the cover for connecting means of the attachment under form of an external thread.

5. The coupling device according to claim 2, wherein an external thread as engagement means of said aerator is made in the lower cylindrical portion for connecting means of the attachment in the form of an internal thread.

6. The coupling device according to claim 2, wherein said flange is provided at the bottom with anti-rotation means to prevent its rotation with respect to said stepped portion of said cylindrical aerator housing.

7. The coupling device according to claim 6, in which adjusting disks equipped with anti-rotation means are interposed between said flange and said stepped portion of said cylindrical aerator housing.

8. The coupling device according to claim 1, wherein said aerator holder fitting superiorly has an annular protrusion adapted to be retained between said faucet mouth, and said cylindrical aerator housing with the interposition of an annular gasket.

9. A coupling device for connecting a water powered apparatus to a faucet having a mouth to which a cylindrical aerator housing having a stepped portion is mounted, the coupling device comprising:
  an aerator, which is located inside the cylindrical aerator housing, the aerator including
    i) an upper cylindrical portion,
    ii) a lower cylindrical portion,
    iii) arms that join the upper cylindrical portion to the lower cylindrical portion, the arms converging in a water flow direction, and
    iv) ventilation openings located between the arms, the ventilation openings for aerating flowing water;
  an aerator holder fitting mounted inside the cylindrical aerator housing resting on the stepped portion of the cylindrical aerator housing;
  engagement means integral with the aerator holder fitting; and
  an attachment for water powered apparatus,
  said attachment for water powered apparatus including connecting means for coupling with the engagement means of the aerator holder fitting,
  wherein a top of said aerator is provided with a flange which is sustained by the aerator holder fitting supported by the stepped portion of said cylindrical aerator housing,
  wherein said aerator holder fitting includes the engagement means that couples to said connecting means of the attachment for water powered apparatus, and
  wherein said engagement means of the aerator holder fitting are a plurality of radial projections facing radially inward, and said connecting means of the attachment for water powered apparatus are in the form of L-shaped grooves.

10. The coupling device according to claim 9, wherein the aerator has a cover which is equipped at the top with a flange for resting on said portion step of cylindrical aerator housing and extends downward from said upper cylindrical portion and externally concentrical to said lower cylindrical portion.

11. The coupling device according to claim 10, wherein said lower cylindrical portion and the cover are connected at the bottom by a circular crown that is concave downward and is provided with a plurality of through holes having vertical axis, radial pins being provided protruding inwardly from the lower cylindrical portion of said aerator as engagement means for a bayonet lock with connecting means in the form of corresponding L-shaped grooves formed in a collar of said attachment for water powered apparatus.

12. The coupling device according to claim 10, wherein an internal thread as engagement means of said aerator is made in the cover for connecting means of the attachment under form of an external thread.

13. The coupling device according to claim 10, wherein an external thread as engagement means of said aerator is made in the lower cylindrical portion for connecting means of the attachment in the form of an internal thread.

14. The coupling device according to claim 10, wherein said flange is provided at the bottom with anti-rotation means to prevent its rotation with respect to said stepped portion of said cylindrical aerator housing.

15. The coupling device according to claim 14, in which adjusting disks equipped with anti-rotation means are interposed between said flange and said stepped portion of said cylindrical aerator housing.

16. The coupling device according to claim 9, wherein said aerator holder fitting superiorly has an annular protrusion adapted to be retained between said faucet mouth, and said cylindrical aerator housing with the interposition of an annular gasket.

\* \* \* \* \*